US012733879B2

(12) United States Patent
Kim et al.

(10) Patent No.: US 12,733,879 B2
(45) Date of Patent: Sep. 15, 2026

(54) COMPUTER DEVICE FOR FAST STIMULATION ARTIFACT TEMPLATE-BASED REAL-TIME STIMULATION ARTIFACT REMOVAL AND METHOD THEREOF

(71) Applicant: Korea Advanced Institute of Science and Technology, Daejeon (KR)

(72) Inventors: Chul Kim, Daejeon (KR); Geunchang Seong, Daejeon (KR)

(73) Assignee: KOREA ADVANCED INSTITUTE OF SCIENCE AND TECHNOLOGY, Daejeon (KR)

(*) Notice: Subject to any disclaimer, the term of this patent is extended or adjusted under 35 U.S.C. 154(b) by 988 days.

(21) Appl. No.: 17/979,535

(22) Filed: Nov. 2, 2022

(65) Prior Publication Data

US 2023/0363719 A1 Nov. 16, 2023

(30) Foreign Application Priority Data

May 12, 2022 (KR) ........................ 10-2022-0058261

(51) Int. Cl.
*A61B 5/00* (2006.01)

(52) U.S. Cl.
CPC .......... *A61B 5/7217* (2013.01); *A61B 5/4848* (2013.01); *A61B 5/725* (2013.01)

(58) Field of Classification Search
CPC ..... A61B 5/7217; A61B 5/4848; A61B 5/725; A61B 5/24; A61B 5/383; A61B 5/7225; A61B 5/4836; A61B 5/7203; A61N 1/36
See application file for complete search history.

(56) References Cited

FOREIGN PATENT DOCUMENTS

| | | | | |
|---|---|---|---|---|
| CN | 112826510 A | * | 5/2021 | ........... A61B 5/6846 |
| KR | 10-2013-0119620 A | | 11/2013 | |

OTHER PUBLICATIONS

Mena, et al., "Electrical stimulus artifact cancellation and neural spike detection on large multi-electrode arrays", Computational Biology, Nov. 13, 2017, 33 pages.

* cited by examiner

*Primary Examiner* — Sana Sahand
(74) *Attorney, Agent, or Firm* — ArentFox Schiff LLP; Joseph M. Maraia

(57) ABSTRACT

Provided are a computer device for fast stimulation artifact template-based real-time stimulation artifact removal and a method thereof. The computer device may be connected to a recording device in which data representing effect of stimulation on a living body is recorded and may be configured to generate a stimulation artifact template for the stimulation based on the recorded data, and to remove a stimulation artifact according to the stimulation from the recorded data using the stimulation artifact template.

14 Claims, 5 Drawing Sheets

FIG. 5

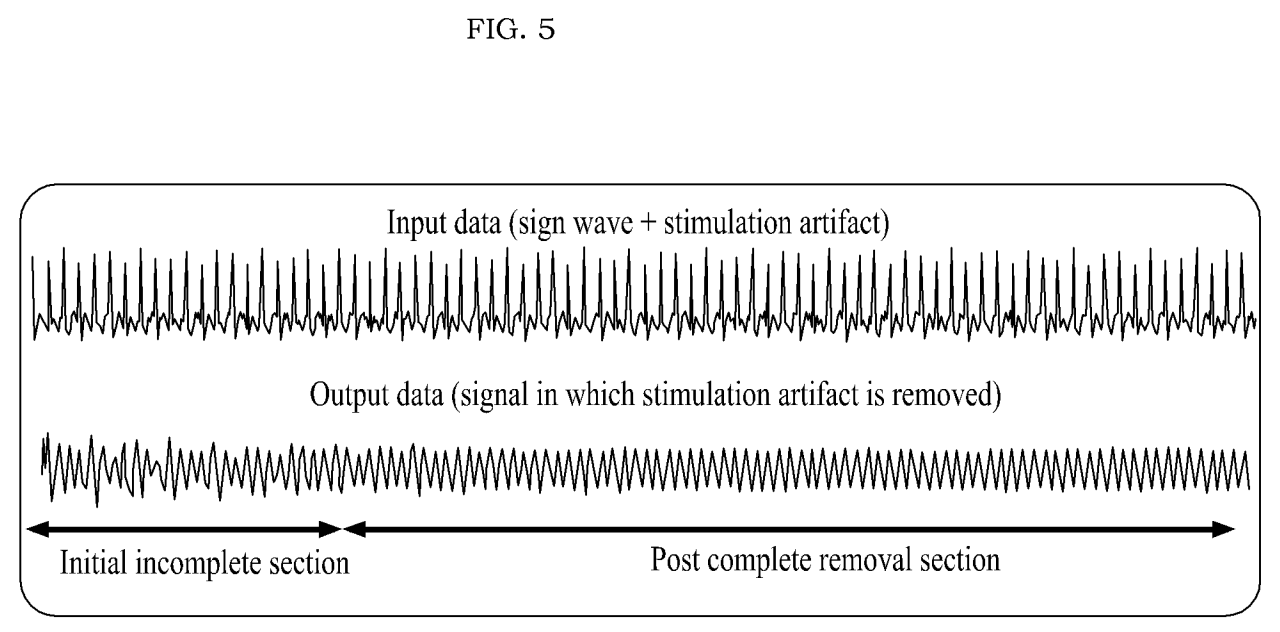

Input data (sign wave + stimulation artifact)

Output data (signal in which stimulation artifact is removed)

Initial incomplete section

Post complete removal section

COMPUTER DEVICE FOR FAST STIMULATION ARTIFACT TEMPLATE-BASED REAL-TIME STIMULATION ARTIFACT REMOVAL AND METHOD THEREOF

CROSS-REFERENCE TO RELATED APPLICATION

This application claims the priority benefit of Korean Patent Application No. 10-2022-0058261, filed on May 12, 2022, in the Korean Intellectual Property Office, the disclosure of which is incorporated herein by reference.

BACKGROUND

1. Field of the Invention

The following description of example embodiments relates to a computer device for fast stimulation artifact template-based real-time stimulation artifact removal and a method of the computer device.

2. Description of the Related Art

Cells that generate electrical signals, such as nerve cells, are involved in the basis of various reactions in vivo. Such biosignals are classified into electrocardiogram (ECG), electromyogram, (EMG), electroencephalogram (EEG), electrocorticogram (ECoG), and the like, according to a measurement target and a measurement location, and used as an important method to analyze biometric information. A method of applying an electrical stimulation to a living body is frequently used to induce medical effect or to study an in-vivo reaction. A closed-loop stimulation method that simultaneously performs stimulation and recording is being actively studied to analyze the effect of electrical stimulation and to find a more effective stimulation method.

A biggest stumbling point of the closed-loop stimulation method lies in that biosignals are contaminated by stimulation signals. In general, stimulation artifact caused by a stimulation signal may have a size of several 100 mV or more compared to a biosignal having a size of several mV or less. In many cases, employed is either a method of deleting data in a section contaminated with a stimulation signal or a method of removing only stimulation artifact from recorded data using an algorithm, such as an independent component analysis (ICA) in a large high-performance processing device (e.g., a PC) outside the recording device.

However, in the first case, there is an issue that biosignal information may not be acquired during a stimulation section and in the second case, there is an issue that a large time delay from a recording point in time to an analysis point in time occurs due to a communication process from the recording device to the high-performance processing device. The first issue may be a big issue since a significant amount of data needs to be discarded if a stimulation is repeated several times for a relatively short period of time due to residual artifact that may remain for a long period of time (several ms) even after the end of stimulation. The second issue may be a big issue since the performance of stimulation treatment may be degraded in that a real-time operation is impossible in the case of medical equipment that needs to sensitively respond to a state of a stimulation target to control the stimulation.

SUMMARY

Example embodiments relate to complementing the issues found in the existing stimulation artifact removal method in two aspects, that is, biometric data preservation and real-time artifact processing. The existing artifact removal method has an issue in that information of a stimulation section may be lost or a great delay may occur in processing data. However, the example embodiments may solve the above issue using a small low-performance digital processing device that operates through direct connection to a recording device and a stimulation artifact removal algorithm to be applied to the corresponding device.

Example embodiments provide a computer device for fast stimulation artifact template-based real-time stimulation artifact removal and a method thereof.

According to an aspect of at least one example embodiment there is provided a computer device connected to a recording device in which data representing effect of stimulation on a living body is recorded, the computer device including a stimulation artifact template generation module configured to generate a stimulation artifact template for the stimulation based on the recorded data; and a stimulation artifact removal module configured to remove a stimulation artifact according to the stimulation from the recorded data using the stimulation artifact template.

According to an aspect of at least one example embodiment, there is provided a method of a computer device connected to a recording device in which data representing effect of stimulation on a living body is recorded, the method including generating a stimulation artifact template for the stimulation based on the recorded data; and removing a stimulation artifact according to the stimulation from the recorded data using the stimulation artifact template.

According to some example embodiments, a computer device may be implemented as a small real-time stimulation artifact removal device and may improve performance of a closed-loop stimulation method. Here, the computer device may outperform disadvantages of a stimulation artifact template-based method, for example, accuracy and template generation time by automatically adjusting a variable and automatically controlling a learning rate. The example embodiments may improve the performance of an electrical stimulation method, widely used in healthcare, games, medical fields such as nerve regeneration, sports fields such as muscle stimulation, digital therapeutics, and basic research, and may provide a new opportunity.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

These and/or other aspects, features, and advantages of the invention will become apparent and more readily appreciated from the following description of embodiments, taken in conjunction with the accompanying drawings of which:

FIG. 5 illustrates an example of effect of a computer device according to various example embodiments.

DETAILED DESCRIPTION

Figure 1:
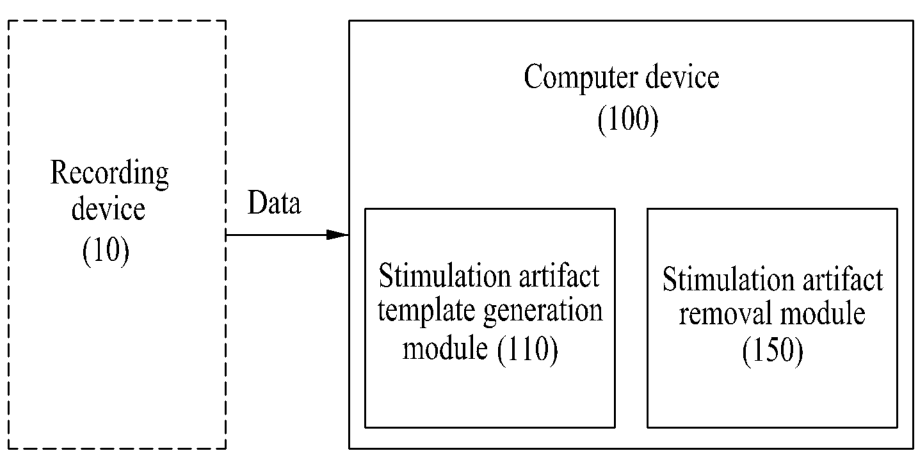
FIG. 1 is a diagram illustrating a configuration of a computer device according to various example embodiments.

Hereinafter, some example embodiments will be described in detail with reference to the accompanying drawings. The following detailed structural or functional description of example embodiments is provided as an example only and various alterations and modifications may be made to the example embodiments. Accordingly, the example embodiments are not construed as being limited to the disclosure and should be understood to include all changes, equivalents, and replacements within the technical scope of the disclosure.

The terminology used herein is for describing various example embodiments only, and is not to be used to limit the disclosure. The singular forms "a," "an," and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Terms, such as first, second, and the like, may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component, without departing from the scope of the disclosure.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Hereinafter, example embodiments are described with reference to the accompanying drawings.

Figure 2:
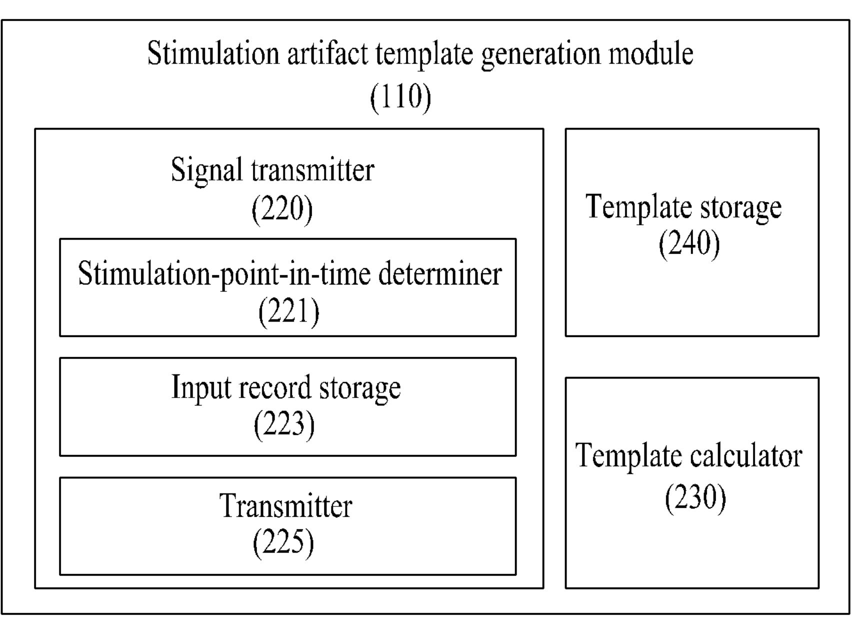
FIG. 2 is a diagram illustrating a configuration of a stimulation artifact template generation module of FIG. 1.

FIG. 1 is a diagram illustrating a configuration of a computer device 100 according to various example embodiments, and FIG. 2 is a diagram illustrating a configuration of a stimulation artifact template generation module 110 of FIG. 1.

Referring to FIG. 1, the computer device 100 relates to removing stimulation artifact and may be a small low-performance digital processing device connectable to a recording device 10 and to which a real-time artifact removal algorithm is applied. Here, data representing effect of stimulation on a living body may be recorded in the recording device 10. In detail, the computer device 100 may include a stimulation artifact template generation module 110 and a stimulation artifact removal module 150. In some example embodiments, the stimulation artifact template generation module 110 and the stimulation artifact removal module 150 may be implemented as a single algorithm or may be implemented as separate algorithms, respectively.

The stimulation artifact template generation module 110 may be configured to generate a stimulation artifact template for a stimulation based on data recorded in the recording device 10. In detail, referring to FIG. 2, the stimulation artifact template generation module 110 may include a signal transmitter 220, a template calculator 230, and a template storage 240.

The signal transmitter 220 may verify a stimulation point in time and may transmit data corresponding to a predetermined time from the stimulation point in time to the template calculator 230. In detail, the signal transmitter 220 may include a stimulation-point-in-time determiner 221, an input record storage 223, and a transmitter 225.

The stimulation-point-in-time determiner 221 may determine the stimulation point in time, that is, a point in time at which the stimulation is applied to the living body from the recorded data. The stimulation-point-in-time determiner 221 may be implemented using a plurality of methods. For example, the stimulation-point-in-time determiner 221 may be configured to receive a stimulation start signal from an external electrical stimulator and, in response thereto, verify the stimulation point in time. As another example, the stimulation-point-in-time determiner 221 may be configured to verify a point at which a gradient of an internally recorded voltage signal changes to be greater than a known voltage variance of a target biosignal and to verify a stimulation point in time corresponding thereto.

The input record storage 223 may receive and store data corresponding to the predetermined time from the stimulation point in time in the recorded data from the recording device 10. In the input record storage 223, a size of a storage space required may vary according to an implementation method of the stimulation-point-in-time determiner 221 and a sampling rate of the recording device 10. The input record storage 223 requires at least a storage space N corresponding to a length acquired by multiplying a time difference between an actual stimulation point in time (t1) and a stimulation point in time (t2) verified by the stimulation-point-in-time determiner 221 by a sampling rate (fs) of the recording device 10 according to the following Equation 1. This is to generate a template based on recording of the entire intact stimulation section.

$$N=(t1-t2)*fs,\ (t1\geq t2)$$

$$N=1,\ (t1<t2) \qquad \text{[Equation 1]}$$

In Equation 1, a unit of N denotes the number of bits of single piece of input data.

The transmitter 225 may transmit the data stored in the input record storage 223 to the template calculator 230. Here, the transmitter 225 may transmit the stored data by each one sample starting from an old signal.

The template calculator 230 may calculate the stimulation artifact template based on the data transmitted from the signal transmitter 220. Through this, the template calculator 230 may calculate the stimulation artifact template based on the stimulation point in time. An in-vivo environment constantly changes, which causes a waveform of stimulation artifact generated from a stimulation signal to vary. However, since a frequency of the stimulation signal is generally much faster, the waveform of the stimulation artifact may be constant within a certain period of time. On the other hand, a biosignal has a random property and thus, when averaging is performed on a predetermined section based on the stimulation point in time, the biosignal disappears and only the stimulation artifact remains. Meanwhile, when a previously stored stimulation artifact template is present in the template storage 240, the template calculator 230 may calculate the stimulation artifact template by applying a variable, that is, K for updating the stored stimulation artifact template. For example, the template calculator 230 may calculate the stimulation artifact template in a form of an infinite impulse response (IIR) filter by summing (1−K) times of the stored stimulation artifact template and K of the data transmitted from the signal transmitter 220. Here, $0 \leq K \leq 1$. Here, the template calculator 230 may track a change in stimulation artifact templates consecutively calculated, and may adjust the variable, that is, K based on the change.

In some example embodiments, to improve device performance, the more constant the waveform of the stimulation artifact is, the better stimulation or recording technology may be introduce for this purpose. For example, a method of more accurately recording a stimulation waveform through an oversampling recording device or maintaining a sampling point in time of the stimulation waveform by synchronizing a stimulator timing and a sampling timing of the recording device may be used.

Since the latest data is updated by K for each stimulation, a size of the stimulation artifact template increases or decreases a little when the template converges. However, if the template has not yet converged, the size has tendency to continue to increase or decrease. Therefore, when the change in the stimulation artifact templates is tracked and shows a tendency to increase or decrease a predetermined number of times or more, a template generation time may be reduced by adjusting K to a larger value such that the template may quickly converge to a larger step size. In other cases, the accuracy may be improved by adjusting again K to a smaller value to reduce the step size and by generating a sophisticated stimulation artifact template within a faster time.

The template storage 240 may be configured to store the stimulation artifact template.

The stimulation artifact removal module 150 may remove the stimulation artifact according to the stimulation from the recorded data using the stored stimulation artifact template. That is, the stimulation artifact removal module 150 may subtract the stimulation artifact template from the recorded data and may recover a biosignal in which the stimulation artifact is removed from the recorded data.

Here, in the recorded data, data not stored in the input record storage 223 is data without stimulation, that is, stimulation-free data. Therefore, the signal transmitter 220 may transmit the corresponding data to the stimulation artifact removal module 150. Through this, the stimulation artifact removal module 150 may output the transmitted data as is.

Figure 3:
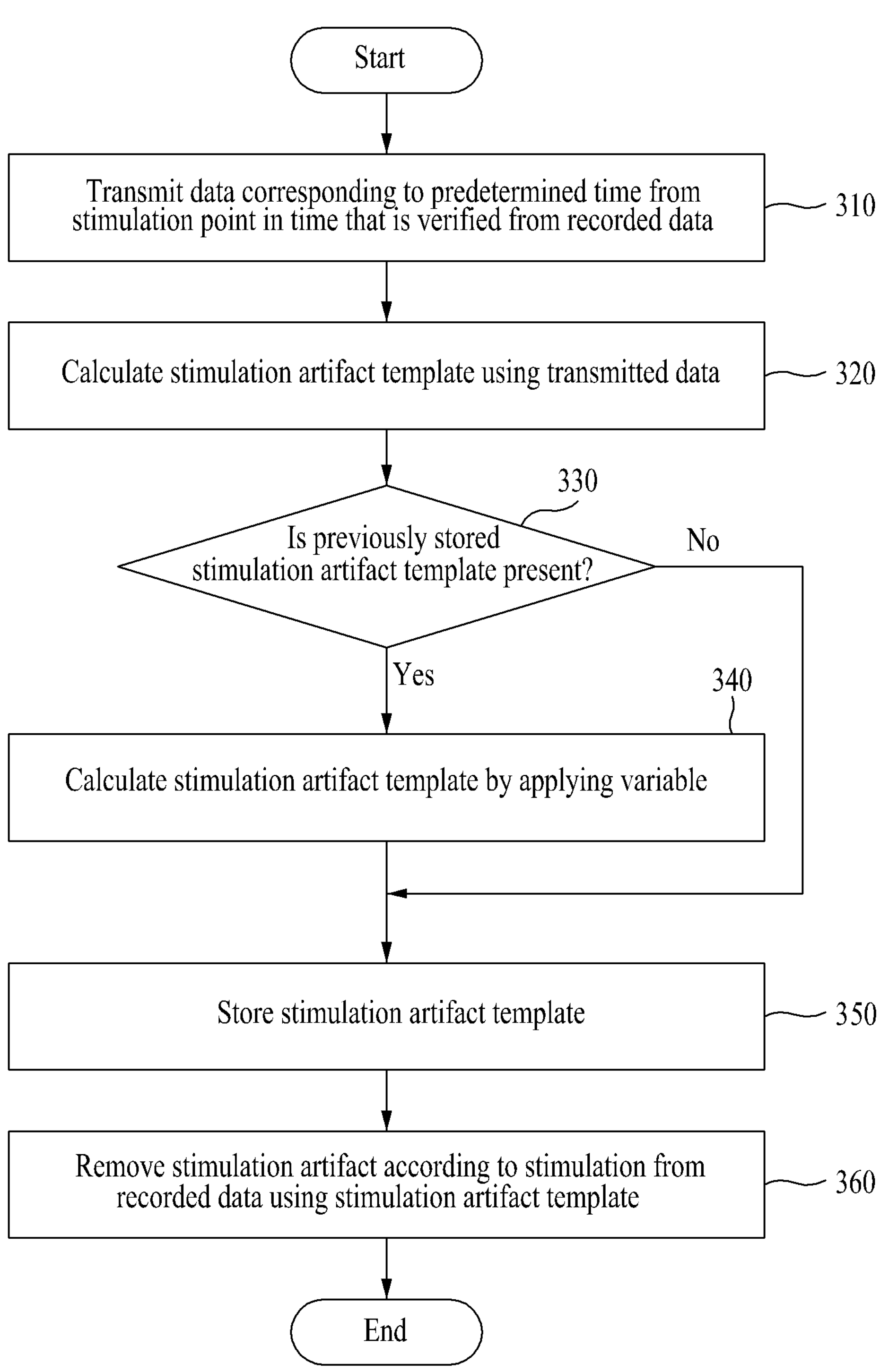
FIG. 3 is a flowchart illustrating a method of a computer device according to various example embodiments.
Figure 4:
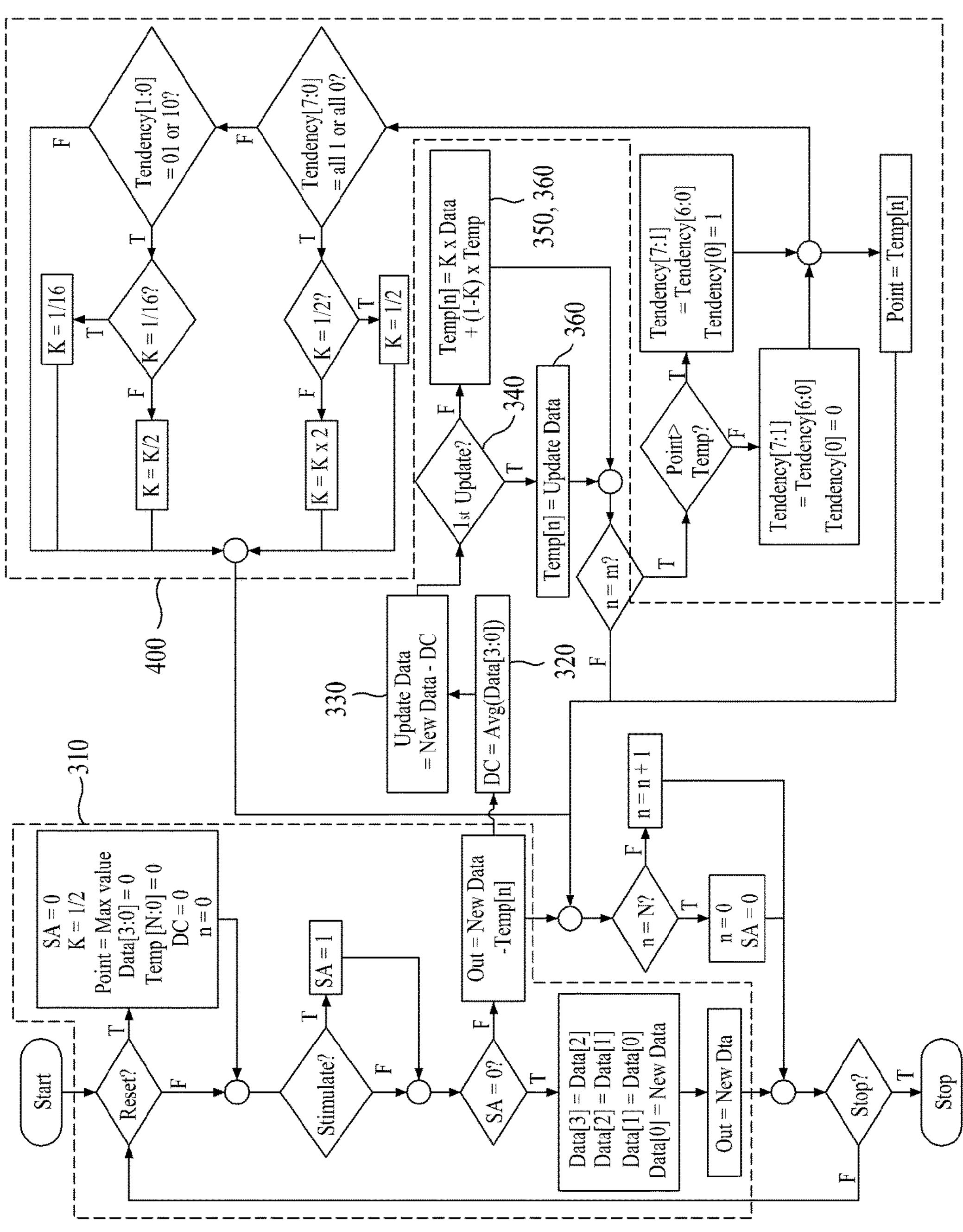
FIG. 4 is a flowchart illustrating operations of FIG. 3.

FIG. 3 is a flowchart illustrating a method of the computer device 100 according to various example embodiments, and FIG. 4 is a flowchart illustrating operations of FIG. 3. Here, FIG. 4 may represent an algorithm of the stimulation artifact template generation module 110.

Referring to FIG. 3, in operation 310, the stimulation artifact template generation module 110 of the computer device 100 may transmit data corresponding to a predetermined time from a stimulation point in time that is verified from recorded data, that is, starting from the stimulation point in time. In detail, the signal transmitter 220 may verify the stimulation point in time and may transmit data corresponding to the predetermined time from the stimulation point in time to the template calculator 230. Here, referring to FIG. 4, the signal transmitter 220 may transmit the data corresponding to the predetermined time from the stimulation point in time to the template calculator 230 and, here, since remaining data is data without stimulation, the signal transmitter 220 may transmit the corresponding data to the stimulation artifact removal module 150. In some example embodiments, the signal transmitter 220 may additionally transmit, to the template calculator 230, data corresponding to a previous time by a corresponding time difference from the verified stimulation point in time using a time difference between an actual stimulation point in time and the verified stimulation point in time.

In operation 320, the stimulation artifact template generation module 110 of the computer device 100 may calculate the stimulation artifact template using the transmitted data. In detail, in operation 320, the template calculator 230 may calculate the stimulation artifact template in a form of an IIR filter from the transmitted data. Through this, the template calculator 230 may calculate the stimulation artifact template based on the stimulation point in time.

In operation 330, the stimulation artifact template generation module 110 of the computer device 100 may determine whether a previously stored stimulation artifact template is present. In detail, whether the previously stored stimulation artifact template is present in the template storage 240 may be determined.

When the previously stored stimulation artifact template is determined to be absent in operation 330, the stimulation artifact template generation module 110 of the computer device 100 may perform operation 350. In operation 350, the stimulation artifact template generation module 110 of the computer device 100 may store the stimulation artifact template calculated in operation 320. That is, the template storage 240 may store the stimulation artifact template calculated by the template calculator 230.

Meanwhile, when the previously stored stimulation artifact template is determined to be present in operation 330, the stimulation artifact template generation module 110 of the computer device 100 may perform operation 340. In operation 340, the stimulation artifact template generation module 110 of the computer device 100 may calculate the stimulation artifact template by applying a variable for updating the stored stimulation artifact template. In detail, the template calculator 230 may calculate the stimulation artifact template by applying the variable, that is, K. For example, the template calculator 230 may calculate the stimulation artifact template in a form of an IIR filter by summing (1−K) times of the stored stimulation artifact template and K of the data transmitted from the signal transmitter 220. Here, K may be greater than or equal to 0 and less than or equal to 1. Then, the stimulation artifact template generation module 110 of the computer device 100 may proceed with operation 350. In operation 350, the stimulation artifact template generation module 110 of the computer device 100 may store the stimulation artifact template calculated in operation 340. That is, the template storage 240 may store the stimulation artifact template calculated by the template calculator 230. Here, the previously stored stimulation artifact template may be updated with the stimulation artifact template calculated by the template calculator 230.

In operation 360, the stimulation artifact removal module 150 of the computer device 100 may remove the stimulation artifact according to the stimulation from the recorded data using the stimulation artifact template. That is, the stimulation artifact removal module 150 may subtract the stimulation artifact template from the recorded data and may recover a biosignal in which the stimulation artifact is removed from the recorded data. Here, referring to FIG. 4, in the case of data transmitted from the signal transmitter

220, that is, stimulation-free data, the stimulation artifact removal module 150 may output the corresponding data as is.

In addition, although not illustrated in FIG. 3, the stimulation artifact removal module 150 of the computer device 100 may adjust the variable, that is, K in operation 400 of FIG. 4. Here, the template calculator 230 may track a change in stimulation artifact templates continuously calculated and may adjust the variable, that is, K based on the change.

FIG. 5 illustrates an example of effect of the computer device 100 according to various example embodiments. Here, FIG. 5 shows an in-vitro experimental result.

Referring to FIG. 5, the computer device 100 may remove stimulation artifact in input data, which may lead to generating output data. The input data may include a signal that includes a sign wave for a biosignal and stimulation artifact and the output data may include a signal in which the stimulation artifact is removed from the input data. Although an initial incomplete section is present in the output data, a post complete removal section in which the stimulation artifact is completely removed through a continuous operation of the computer device 100 may be stable.

For example, the example embodiments provide the computer device 100 for fast stimulation artifact template-based real-time stimulation artifact removal and a method of the computer device 100. According to some example embodiments, the computer device 100 may be implemented as a small real-time stimulation artifact removal device and may improve performance of a closed-loop stimulation method. Here, the computer device 100 may outperform disadvantages of a stimulation artifact template-based method, for example, accuracy and template generation time, by automatically adjusting a variable and automatically controlling a learning rate. The example embodiments may improve the performance of an electrical stimulation method, widely used in healthcare, games, medical fields such as nerve regeneration, sports fields such as muscle stimulation, digital therapeutics, and basic research, and may provide a new opportunity.

According to example embodiments, the computer device 100 may be connected to the recording device 10 in which data representing effect of stimulation on a living body is recorded, and may include the stimulation artifact template generation module 110 configured to generate a stimulation artifact template for the stimulation based on the recorded data; and the stimulation artifact removal module 150 configured to remove a stimulation artifact according to the stimulation from the recorded data using the stimulation artifact template.

According to example embodiments, the stimulation artifact template generation module 110 may include the signal transmitter 220 configured to verify a stimulation point in time from the recorded data and to transmit data corresponding to a predetermined time from the stimulation point in time; the template calculator 230 configured to calculate the stimulation artifact template from the transmitted data; and the template storage 240 configured to store the stimulation artifact template.

According to example embodiments, the template calculator 230 may be configured to calculate the stimulation artifact template in a form of an infinite impulse response (IIR) filter.

According to example embodiments, the template calculator 230 may be configured to, when a previously stored stimulation artifact template is present in the template storage 240, calculate the stimulation artifact template by applying a variable for updating the stored stimulation artifact template. According to example embodiments, the template calculator 230 may be configured to, when the variable is K, calculate the stimulation artifact template by summing (1−K) times of the stored stimulation artifact template and K of the transmitted data.

According to example embodiments, the template calculator 230 may be configured to track a change in stimulation artifact templates consecutively calculated, and to adjust the variable based on the change.

According to example embodiments, the variable may be greater than or equal to 0 and less than or equal to 1.

According to example embodiments, the signal transmitter 220 may include the stimulation-point-in-time determiner 221 configured to verify the stimulation point in time from the recorded data; the input record storage 223 configured to receive and store the data corresponding to the predetermined time from the stimulation point in time from the recording device 10; and the transmitter 225 configured to transmit the stored data to the template calculator 230.

According to example embodiments, the stimulation artifact removal module 150 may be configured to subtract the stimulation artifact template from the recorded data and to recover a biosignal in which the stimulation artifact is removed from the recorded data.

According to example embodiments, the computer device 100 may be connected to the recording device 10 in which data representing effect of stimulation on a living body is recorded and a method of the computer device 100 may include generating a stimulation artifact template for the stimulation based on the recorded data; and removing a stimulation artifact according to the stimulation from the recorded data using the stimulation artifact template.

According to example embodiments, the generating of the stimulation artifact template may include transmitting, by the signal transmitter 220, data corresponding to a predetermined time from a stimulation point in time that is verified from the recorded data; calculating, by the template calculator 230, the stimulation artifact template from the transmitted data; and storing, by the template storage 240, the stimulation artifact template.

According to example embodiments, the calculating of the stimulation artifact template may include calculating the stimulation artifact template in a form of an IIR filter.

According to example embodiments, the calculating of the stimulation artifact template may include, when a previously stored stimulation artifact template is present in the template storage 240, calculating the stimulation artifact template by applying a variable for updating the stored stimulation artifact template.

According to example embodiments, the calculating of the stimulation artifact template by applying the variable may include, when the variable is K, calculate the stimulation artifact template by summing (1−K) times of the stored stimulation artifact template and K of the transmitted data.

According to example embodiments, the template calculator 230 may be configured to track a change in stimulation artifact templates consecutively calculated, and to adjust the variable based on the change.

According to example embodiments, the variable may be greater than or equal to 0 and less than or equal to 1.

According to example embodiments, the removing of the stimulation artifact may include subtracting the stimulation artifact template from the recorded data and recovering a biosignal in which the stimulation artifact is removed from the recorded data.

The apparatuses described herein may be implemented using hardware components, software components, and/or a combination of the hardware components and the software components. For example, a processing device and components described herein may be implemented using one or more general-purpose or special purpose computers, for example, a processor, a controller, an arithmetic logic unit (ALU), a digital signal processor, a microcomputer, a field programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of the processing device is used as singular; however, one skilled in the art will be appreciated that the processing device may include multiple processing elements and/or multiple types of processing elements. For example, the processing device may include multiple processors or a processor and a controller. In addition, other processing configurations are possible, such as parallel processors.

The software may include a computer program, a piece of code, an instruction, or some combinations thereof, for independently or collectively instructing or configuring the processing device to operate as desired. Software and/or data may be embodied in any type of machine, component, physical equipment, computer storage medium or device, to provide instructions or data to the processing device or be interpreted by the processing device. The software also may be distributed over network coupled computer systems so that the software is stored and executed in a distributed fashion. The software and data may be stored by one or more computer readable storage mediums.

The methods according to various example embodiments may be implemented in a form of a program instruction executable through various computer methods and recorded in computer-readable media. Here, the media may be to continuously store a computer-executable program or to temporarily store the same for execution or download. The media may be various types of record methods or storage methods in which single hardware or a plurality of hardware is combined and may be distributed over a network without being limited to a medium that is directly connected to a computer system. Examples of the media include magnetic media such as hard disks, floppy disks, and magnetic tapes; optical media such as CD ROM and DVD; magneto-optical media such as floptical disks; and hardware devices that are specially configured to store and perform program instructions, such as read-only memory (ROM), random access memory (RAM), flash memory, and the like. Examples of other media may include recording media and storage media managed by an app store that distributes applications or a site, a server, and the like that supplies and distributes other various types of software.

Various example embodiments and the terms used herein are not construed to limit description disclosed herein to a specific implementation and should be understood to include various modifications, equivalents, and/or substitutions of a corresponding example embodiment. In the drawings, like reference numerals refer to like components throughout the present specification. The singular forms "a," "an," and "the" are intended to include the plural forms as well, unless the context clearly indicates otherwise. Herein, the expressions, "A or B," "at least one of A and/or B," "A, B, or C," "at least one of A, B, and/or C," and the like may include any possible combinations of listed items. Terms "first," "second," etc., are used to describe corresponding components regardless of order or importance and the terms are simply used to distinguish one component from another component. The components should not be limited by the terms. When a component (e.g., a first component) is described to be "(functionally or communicatively) connected to" or "accessed to" another component (e.g., a second component), the component may be directly connected to the other component or may be connected through still another component (e.g., a third component).

The term "module" used herein may include a unit configured as hardware, software, or firmware, and may be interchangeably used with the terms, for example, "logic," "logic block," "part," "circuit," etc. The module may be an integrally configured part, a minimum unit that performs at least function, or a portion thereof. For example, the module may be configured as an application-specific integrated circuit (ASIC).

According to various example embodiments, each of the components (e.g., module or program) may include a singular object or a plurality of objects. According to various example embodiments, at least one of the components or operations may be omitted. Alternatively, at least one another component or operation may be added. Alternatively or additionally, a plurality of components (e.g., module or program) may be integrated into a single component. In this case, the integrated component may perform one or more functions of each of the components in the same or similar manner as it is performed by a corresponding component before integration. According to various example embodiments, operations performed by a module, a program, or another component may be performed in a sequential, parallel, iterative, or heuristic manner. Alternatively, at least one of the operations may be performed in different sequence or omitted. Alternatively, at least one another operation may be added.

What is claimed is:

1. A computer device connected to a recording device in which data representing effect of stimulation configured for a living body is recorded, the computer device comprising:
- a stimulation artifact template generation module configured to generate a stimulation artifact template for the stimulation based on the recorded data; and
- a stimulation artifact removal module configured to remove a stimulation artifact according to the stimulation from the recorded data using the stimulation artifact template,
- wherein the stimulation artifact template generation module comprises:
  - a signal transmitter configured to verify a stimulation point in time from the recorded data and to transmit data corresponding to a predetermined time from the stimulation point in time;
  - a template calculator configured to calculate the stimulation artifact template from the transmitted data; and
  - a template storage configured to store the stimulation artifact template,
- wherein the template calculator is configured to:
  - when a previously stored stimulation artifact template is present in the template storage, calculate the stimulation artifact template by summing a value of the previously stored stimulation artifact template multiplied by (1-K) and a value of the transmitted data multiplied by K, wherein K is a variable for updating the stored stimulation artifact template;
  - track a change in stimulation artifact templates consecutively calculated; and
  - adjust the variable K based on the change.

2. The computer device of claim 1, wherein the template calculator is configured to calculate the stimulation artifact template in a form of an infinite impulse response (IIR) filter.

3. The computer device of claim 1, wherein the variable K is greater than or equal to 0 and less than or equal to 1.

4. The computer device of claim 1, wherein the signal transmitter comprises:

a stimulation-point-in-time determiner configured to perform the verification of the stimulation point in time from the recorded data;

an input record storage configured to receive and store the data corresponding to the predetermined time from the stimulation point in time from the recording device; and a transmitter configured to transmit the stored data to the template calculator.

5. The computer device of claim 1, wherein the stimulation artifact removal module is configured to subtract the stimulation artifact template from the recorded data and to recover a biosignal in which the stimulation artifact is removed from the recorded data.

6. The computer device of claim 1, wherein the template calculator is configured to:

increase the variable K when the change indicates a consecutive increase or a consecutive decrease for a predetermined number of times or more; and decrease the variable K in other cases.

7. A method of a computer device connected to a recording device in which data representing effect of stimulation configured for a living body is recorded, the method comprising:

generating a stimulation artifact template for the stimulation based on the recorded data; and removing a stimulation artifact according to the stimulation from the recorded data using the stimulation artifact template, wherein the generating of the stimulation artifact template comprises:

transmitting, by a signal transmitter, data corresponding to a predetermined time from a stimulation point in time that is verified from the recorded data;

calculating, by a template calculator, the stimulation artifact template from the transmitted data; and storing, by a template storage, the stimulation artifact template, wherein the calculating of the stimulation artifact template comprises:

when a previously stored stimulation artifact template is present in the template storage, calculating the stimulation artifact template by summing a value of the previously stored stimulation artifact template multiplied by (1-K) and a value of the transmitted data multiplied by K, wherein K is a variable for updating the stored stimulation artifact template;

tracking a change in stimulation artifact templates consecutively calculated; and adjusting the variable K based on the change.

8. The method of claim 7, wherein the calculating of the stimulation artifact template comprises calculating the stimulation artifact template in a form of an infinite impulse response (IIR) filter.

9. The method of claim 7, wherein the variable K is greater than or equal to 0 and less than or equal to 1.

10. The method of claim 7, wherein the removing of the stimulation artifact comprises subtracting the stimulation artifact template from the recorded data and recovering a biosignal in which the stimulation artifact is removed from the recorded data.

11. The method of claim 7, wherein the adjusting of the variable K based on the change comprises:

increasing the variable K when the change indicates a consecutive increase or a consecutive decrease for a predetermined number of times or more; and decreasing the variable K in other cases.

12. A non-transitory computer-readable recording medium storing a computer program to implement a method in a computer device connected to a recording device in which data representing effect of stimulation configured for a living body is recorded, wherein the method comprises:

generating a stimulation artifact template for the stimulation based on the recorded data; and removing a stimulation artifact according to the stimulation from the recorded data using the stimulation artifact template, wherein the generating of the stimulation artifact template comprises:

transmitting, by a signal transmitter, data corresponding to a predetermined time from a stimulation point in time that is verified from the recorded data;

calculating, by a template calculator, the stimulation artifact template from the transmitted data; and storing, by a template storage, the stimulation artifact template, wherein the calculating of the stimulation artifact template comprises:

when a previously stored stimulation artifact template is present in the template storage, calculating the stimulation artifact template by summing a value of the previously stored stimulation artifact template multiplied by (1−K) and a value of the transmitted data multiplied by K, wherein K is a variable for updating the stored stimulation artifact template;

tracking a change in stimulation artifact templates consecutively calculated; and adjusting the variable K based on the change.

13. The non-transitory computer-readable recording medium of claim 12, wherein the removing of the stimulation artifact comprises subtracting the stimulation artifact template from the recorded data and recovering a biosignal in which the stimulation artifact is removed from the recorded data.

14. The non-transitory computer-readable recording medium of claim 12, wherein the adjusting of the variable K based on the change comprises:

increasing the variable K when the change a consecutive increase or a consecutive decrease for a predetermined number of times or more; and decreasing the variable K in other cases.

* * * * *